(12) United States Patent
Addison et al.

(10) Patent No.: US 10,357,406 B2
(45) Date of Patent: Jul. 23, 2019

(54) PATTERNED SILICONE COATING

(71) Applicant: KCI USA, INC., San Antonio, TX (US)

(72) Inventors: Deborah Addison, Via Lancaster (GB); Sally Stephens, Skipton (GB); Patrick Joseph Brosnan, Bingley (GB); Gary Street, West Yorkshire (GB); Ian Teet, Kelbrooke (GB); Risham Amjad, Manchester (GB)

(73) Assignee: KCI USA, INC., San Antonio, TX (US)

( * ) Notice: Subject to any disclaimer, the term of this patent is extended or adjusted under 35 U.S.C. 154(b) by 158 days.

(21) Appl. No.: 15/225,536

(22) Filed: Aug. 1, 2016

(65) Prior Publication Data
US 2017/0027761 A1 Feb. 2, 2017

Related U.S. Application Data

(62) Division of application No. 14/111,626, filed as application No. PCT/GB2012/050822 on Apr. 13, 2012, now Pat. No. 9,433,534.

(30) Foreign Application Priority Data

Apr. 15, 2011 (GB) .................................. 1106491.2

(51) Int. Cl.
*A61F 13/02* (2006.01)
*B05D 1/28* (2006.01)
(Continued)

(52) U.S. Cl.
CPC ........ *A61F 13/0283* (2013.01); *A61F 13/025* (2013.01); *A61F 13/0206* (2013.01);
(Continued)

(58) Field of Classification Search
CPC .............. A61L 15/01; B05D 5/10; B07B 1/49
USPC ....................................... 209/399; 427/208.2
See application file for complete search history.

(56) References Cited

U.S. PATENT DOCUMENTS 1,355,846 A 10/1920 Rannells
2,547,758 A 4/1951 Kelling
(Continued)

FOREIGN PATENT DOCUMENTS

AU 550575 B2 3/1986
AU 745271 B2 3/2002
(Continued)

OTHER PUBLICATIONS

M. Waring et al., "Cell attachment to adhesive dressing: qualitative and quantitative analysis", Wounds, UK, (2008), vol. 4, No. 3, pp. 35-47.
(Continued)

*Primary Examiner* — Andrew J Bowman
(74) *Attorney, Agent, or Firm* — Foley & Lardner LLP

(57) ABSTRACT

A method of applying a patterned coating of a silicone adhesive to a substrate sheet, comprising the steps of pattern coating a silicone precursor composition onto the substrate, followed by thermally curing the precursor composition coated on the substrate. The precursor composition is a viscous fluid, and the pattern coating is performed by suitably modified block printing, intaglio printing or screen printing methods. Also provided are coated substrates obtainable by the methods of the invention, and wound dressings comprising such coated substrates.

21 Claims, 3 Drawing Sheets

(51) Int. Cl.
  *C09J 5/06* (2006.01)
  *B05D 1/32* (2006.01)
  *B05D 3/02* (2006.01)
  *C09J 7/38* (2018.01)
  *C09J 7/22* (2018.01)
  *C09J 7/26* (2018.01)
  *C09J 183/04* (2006.01)

(52) U.S. Cl.
  CPC ............ *A61F 13/0276* (2013.01); *B05D 1/28* (2013.01); *B05D 1/322* (2013.01); *B05D 3/0254* (2013.01); *C09J 5/06* (2013.01); *C09J 7/22* (2018.01); *C09J 7/26* (2018.01); *C09J 7/38* (2018.01); *C09J 183/04* (2013.01); *C09J 2201/606* (2013.01); *C09J 2423/106* (2013.01); *C09J 2475/006* (2013.01); *C09J 2483/00* (2013.01); *Y10T 428/24802* (2015.01)

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,172,808 A | 3/1965 | Baumann et al. |
| 3,367,332 A | 2/1968 | Groves |
| 3,376,868 A | 4/1968 | Mondiadis |
| 3,520,300 A | 7/1970 | Flowers, Jr. |
| 3,568,675 A | 3/1971 | Harvey |
| 3,648,692 A | 3/1972 | Wheeler |
| 3,682,180 A | 8/1972 | McFarlane |
| 3,742,952 A | 7/1973 | Magers et al. |
| 3,774,611 A | 11/1973 | Tussey et al. |
| 3,777,016 A | 12/1973 | Gilbert |
| 3,779,243 A | 12/1973 | Tussey et al. |
| 3,826,254 A | 7/1974 | Mellor |
| 3,852,823 A | 12/1974 | Jones |
| 3,967,624 A | 7/1976 | Milnamow |
| 3,983,297 A | 9/1976 | Ono et al. |
| 4,080,970 A | 3/1978 | Miller |
| 4,096,853 A | 6/1978 | Weigand |
| 4,139,004 A | 2/1979 | Gonzalez, Jr. |
| 4,141,361 A | 2/1979 | Snyder |
| 4,163,822 A | 8/1979 | Walter |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,360,015 A | 11/1982 | Mayer |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,414,970 A | 11/1983 | Berry |
| 4,419,097 A | 12/1983 | Rowland |
| 4,465,485 A | 8/1984 | Kashmer et al. |
| 4,468,418 A * | 8/1984 | Freeman .................. B05D 1/28 427/208.2 |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,529,402 A | 7/1985 | Weilbacher et al. |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,652 A | 5/1987 | Weilbacher |
| 4,664,662 A | 5/1987 | Webster |
| 4,710,165 A | 12/1987 | McNeil et al. |
| 4,715,857 A | 12/1987 | Juhasz et al. |
| 4,733,659 A | 3/1988 | Edenbaum et al. |
| 4,743,232 A | 5/1988 | Kruger |
| 4,753,230 A | 6/1988 | Carus et al. |
| 4,758,220 A | 7/1988 | Sundblom et al. |
| 4,787,888 A | 11/1988 | Fox |
| 4,826,494 A | 5/1989 | Richmond et al. |
| 4,832,008 A | 5/1989 | Gilman |
| 4,838,883 A | 6/1989 | Matsuura |
| 4,840,187 A | 6/1989 | Brazier |
| 4,848,364 A | 7/1989 | Bosman |
| 4,863,449 A | 9/1989 | Therriault et al. |
| 4,871,611 A | 10/1989 | LeBel |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,930,997 A | 6/1990 | Bennett |
| 4,941,882 A | 7/1990 | Ward et al. |
| 4,953,565 A | 9/1990 | Tachibana et al. |
| 4,961,493 A | 10/1990 | Kaihatsu |
| 4,969,880 A | 11/1990 | Zamierowski |
| 4,981,474 A | 1/1991 | Bopp et al. |
| 4,985,019 A | 1/1991 | Michelson |
| 4,995,382 A | 2/1991 | Lang et al. |
| 4,996,128 A | 2/1991 | Aldecoa et al. |
| 5,010,883 A | 4/1991 | Rawlings et al. |
| 5,018,515 A | 5/1991 | Gilman |
| 5,037,397 A | 8/1991 | Kalt et al. |
| 5,086,170 A | 2/1992 | Luheshi et al. |
| 5,092,323 A | 3/1992 | Riedel et al. |
| 5,092,858 A | 3/1992 | Benson et al. |
| 5,100,396 A | 3/1992 | Zamierowski |
| 5,112,323 A | 5/1992 | Winkler et al. |
| 5,134,994 A | 8/1992 | Say |
| 5,149,331 A | 9/1992 | Ferdman et al. |
| 5,151,314 A | 9/1992 | Brown |
| 5,152,757 A | 10/1992 | Eriksson |
| 5,167,613 A | 12/1992 | Karami et al. |
| 5,176,663 A | 1/1993 | Svedman et al. |
| 5,180,375 A | 1/1993 | Feibus |
| 5,215,522 A | 6/1993 | Page et al. |
| 5,232,453 A | 8/1993 | Plass et al. |
| 5,261,893 A | 11/1993 | Zamierowski |
| 5,266,372 A | 11/1993 | Arakawa et al. |
| 5,270,358 A | 12/1993 | Asmus |
| 5,278,100 A | 1/1994 | Doan et al. |
| 5,279,550 A | 1/1994 | Habib et al. |
| 5,298,015 A | 3/1994 | Komatsuzaki et al. |
| 5,342,329 A | 8/1994 | Croquevielle |
| 5,342,376 A | 8/1994 | Ruff |
| 5,344,415 A | 9/1994 | DeBusk et al. |
| 5,356,386 A | 10/1994 | Goldberg et al. |
| 5,358,494 A | 10/1994 | Svedman |
| 5,384,174 A | 1/1995 | Ward et al. |
| 5,387,207 A | 2/1995 | Dyer et al. |
| 5,419,769 A | 5/1995 | Devlin et al. |
| 5,423,778 A | 6/1995 | Eriksson et al. |
| 5,429,590 A | 7/1995 | Saito et al. |
| 5,437,622 A | 8/1995 | Carion |
| 5,437,651 A | 8/1995 | Todd et al. |
| 5,445,604 A | 8/1995 | Lang |
| 5,447,492 A | 9/1995 | Cartmell et al. |
| 5,501,212 A | 3/1996 | Psaros |
| 5,522,808 A | 6/1996 | Skalla |
| 5,527,293 A | 6/1996 | Zamierowski |
| 5,549,584 A | 8/1996 | Gross |
| 5,549,585 A | 8/1996 | Maher et al. |

(56) References Cited

U.S. PATENT DOCUMENTS

| | | |
|---|---|---|
| 5,556,375 A | 9/1996 | Ewall |
| 5,585,178 A | 12/1996 | Calhoun et al. |
| 5,599,292 A | 2/1997 | Yoon |
| 5,607,388 A | 3/1997 | Ewall |
| 5,634,893 A | 6/1997 | Rishton |
| 5,636,643 A | 6/1997 | Argenta et al. |
| 5,641,506 A | 6/1997 | Talke et al. |
| 5,645,081 A | 7/1997 | Argenta et al. |
| 5,653,224 A | 8/1997 | Johnson |
| 5,678,564 A | 10/1997 | Lawrence et al. |
| 5,710,233 A | 1/1998 | Meckel et al. |
| 5,714,225 A | 2/1998 | Hansen et al. |
| 5,736,470 A | 4/1998 | Schneberger et al. |
| 5,776,119 A | 7/1998 | Bilbo et al. |
| 5,807,295 A | 9/1998 | Hutcheon et al. |
| 5,919,476 A | 7/1999 | Fischer et al. |
| 5,941,863 A | 8/1999 | Guidotti et al. |
| 5,981,822 A | 11/1999 | Addison |
| 6,071,267 A | 6/2000 | Zamierowski |
| 6,086,995 A | 7/2000 | Smith |
| 6,135,116 A | 10/2000 | Vogel et al. |
| 6,174,306 B1 | 1/2001 | Fleischmann |
| 6,191,335 B1 | 2/2001 | Robinson |
| 6,241,747 B1 | 6/2001 | Ruff |
| 6,262,329 B1 | 7/2001 | Brunsveld et al. |
| 6,287,316 B1 | 9/2001 | Agarwal et al. |
| 6,345,623 B1 | 2/2002 | Heaton et al. |
| 6,458,109 B1 | 10/2002 | Henley et al. |
| 6,488,643 B1 | 12/2002 | Tumey et al. |
| 6,493,568 B1 | 12/2002 | Bell et al. |
| 6,495,229 B1 | 12/2002 | Carte et al. |
| 6,548,727 B1 | 4/2003 | Swenson |
| 6,553,998 B2 | 4/2003 | Heaton et al. |
| 6,566,575 B1 | 5/2003 | Stickels et al. |
| 6,566,577 B1 | 5/2003 | Addison et al. |
| 6,626,891 B2 | 9/2003 | Ohmstede |
| 6,627,215 B1 | 9/2003 | Dale et al. |
| 6,648,862 B2 | 11/2003 | Watson |
| 6,680,113 B1 | 1/2004 | Lucast et al. |
| 6,685,681 B2 | 2/2004 | Lockwood et al. |
| 6,693,180 B2 | 2/2004 | Lee et al. |
| 6,695,823 B1 | 2/2004 | Lina et al. |
| 6,752,794 B2 | 6/2004 | Lockwood et al. |
| 6,787,682 B2 | 9/2004 | Gilman |
| 6,814,079 B2 | 11/2004 | Heaton et al. |
| 6,855,135 B2 | 2/2005 | Lockwood et al. |
| 6,856,821 B2 | 2/2005 | Johnson |
| 6,979,324 B2 | 12/2005 | Bybordi et al. |
| 7,070,584 B2 | 7/2006 | Johnson et al. |
| 7,154,017 B2 | 12/2006 | Sigurjonsson et al. |
| 7,402,721 B2 | 7/2008 | Sigurjonsson et al. |
| 7,569,742 B2 | 8/2009 | Haggstrom et al. |
| 7,645,269 B2 | 1/2010 | Zamierowski |
| 8,298,197 B2 | 10/2012 | Eriksson et al. |
| 8,529,532 B2 | 9/2013 | Pinto et al. |
| 8,632,523 B2 | 1/2014 | Eriksson et al. |
| 8,764,732 B2 | 7/2014 | Hartwell |
| 9,192,444 B2 | 11/2015 | Locke et al. |
| 2001/0030304 A1 | 10/2001 | Kohda et al. |
| 2001/0051178 A1 | 12/2001 | Blatchford et al. |
| 2002/0009568 A1 | 1/2002 | Bries et al. |
| 2002/0016346 A1 | 2/2002 | Brandt et al. |
| 2002/0065494 A1 | 5/2002 | Lockwood et al. |
| 2002/0077661 A1 | 6/2002 | Saadat |
| 2002/0115951 A1 | 8/2002 | Norstrem et al. |
| 2002/0119292 A1 | 8/2002 | Venkatasanthanam et al. |
| 2002/0120185 A1 | 8/2002 | Johnson |
| 2002/0130064 A1* | 9/2002 | Adams .............. B01D 29/012 209/399 |
| 2002/0143286 A1 | 10/2002 | Tumey |
| 2002/0150270 A1 | 10/2002 | Werner |
| 2002/0150720 A1 | 10/2002 | Howard et al. |
| 2002/0161346 A1 | 10/2002 | Lockwood et al. |
| 2002/0164346 A1 | 11/2002 | Nicolette |
| 2002/0183702 A1 | 12/2002 | Henley et al. |
| 2002/0198504 A1 | 12/2002 | Risk et al. |
| 2003/0014022 A1 | 1/2003 | Lockwood et al. |
| 2003/0109855 A1 | 6/2003 | Solem et al. |
| 2003/0158577 A1 | 8/2003 | Ginn et al. |
| 2003/0212357 A1 | 11/2003 | Pace |
| 2003/0225347 A1 | 12/2003 | Argenta et al. |
| 2003/0225355 A1 | 12/2003 | Butler |
| 2004/0002676 A1 | 1/2004 | Siegwart et al. |
| 2004/0030304 A1 | 2/2004 | Hunt et al. |
| 2004/0064132 A1 | 4/2004 | Boehringer et al. |
| 2004/0077984 A1 | 4/2004 | Worthley |
| 2004/0099268 A1 | 5/2004 | Smith et al. |
| 2004/0118401 A1 | 6/2004 | Smith et al. |
| 2004/0127836 A1 | 7/2004 | Sigurjonsson et al. |
| 2004/0127862 A1 | 7/2004 | Bubb et al. |
| 2004/0133143 A1 | 7/2004 | Burton et al. |
| 2004/0186239 A1 | 9/2004 | Qin et al. |
| 2004/0219337 A1 | 11/2004 | Langley et al. |
| 2004/0230179 A1 | 11/2004 | Shehada |
| 2005/0034731 A1 | 2/2005 | Rousseau et al. |
| 2005/0054998 A1 | 3/2005 | Poccia et al. |
| 2005/0059918 A1 | 3/2005 | Sigurjonsson et al. |
| 2005/0065484 A1 | 3/2005 | Watson |
| 2005/0070858 A1 | 3/2005 | Lockwood et al. |
| 2005/0101940 A1 | 5/2005 | Radl et al. |
| 2005/0113732 A1 | 5/2005 | Lawry |
| 2005/0124925 A1 | 6/2005 | Scherpenborg |
| 2005/0131327 A1 | 6/2005 | Lockwood et al. |
| 2005/0137539 A1 | 6/2005 | Biggie et al. |
| 2005/0143694 A1 | 6/2005 | Schmidt et al. |
| 2005/0159695 A1 | 7/2005 | Cullen et al. |
| 2005/0161042 A1 | 7/2005 | Fudge et al. |
| 2005/0163978 A1 | 7/2005 | Strobech et al. |
| 2005/0214376 A1 | 9/2005 | Faure et al. |
| 2005/0233072 A1 | 10/2005 | Stephan et al. |
| 2005/0256437 A1 | 11/2005 | Silcock et al. |
| 2005/0261642 A1 | 11/2005 | Weston |
| 2005/0261643 A1 | 11/2005 | Bybordi et al. |
| 2005/0277860 A1 | 12/2005 | Jensen |
| 2006/0079852 A1 | 4/2006 | Bubb et al. |
| 2006/0083776 A1 | 4/2006 | Bott et al. |
| 2006/0154546 A1 | 7/2006 | Murphy et al. |
| 2006/0241542 A1 | 10/2006 | Gudnason et al. |
| 2006/0271020 A1 | 11/2006 | Huang et al. |
| 2007/0027414 A1 | 2/2007 | Hoffman et al. |
| 2007/0078366 A1 | 4/2007 | Haggstrom et al. |
| 2007/0185426 A1 | 8/2007 | Ambrosio et al. |
| 2007/0225663 A1 | 9/2007 | Watt et al. |
| 2007/0265585 A1 | 11/2007 | Joshi et al. |
| 2007/0265586 A1 | 11/2007 | Joshi et al. |
| 2008/0090085 A1 | 4/2008 | Kawate et al. |
| 2008/0119802 A1 | 5/2008 | Riesinger |
| 2008/0149104 A1 | 6/2008 | Eifler |
| 2008/0195017 A1 | 8/2008 | Robinson et al. |
| 2008/0225663 A1 | 9/2008 | Smith et al. |
| 2008/0243044 A1 | 10/2008 | Hunt et al. |
| 2008/0269657 A1 | 10/2008 | Brenneman et al. |
| 2008/0271804 A1 | 11/2008 | Biggie et al. |
| 2009/0025724 A1 | 1/2009 | Herron, Jr. |
| 2009/0088719 A1 | 4/2009 | Driskell |
| 2009/0093779 A1 | 4/2009 | Riesinger |
| 2009/0124988 A1 | 5/2009 | Coulthard |
| 2009/0177172 A1 | 7/2009 | Wilkes |
| 2009/0216204 A1 | 8/2009 | Bhavaraju et al. |
| 2009/0227969 A1 | 9/2009 | Jaeb et al. |
| 2009/0264807 A1 | 10/2009 | Haggstrom et al. |
| 2009/0292264 A1 | 11/2009 | Hudspeth et al. |
| 2009/0312662 A1 | 12/2009 | Colman et al. |
| 2009/0326488 A1 | 12/2009 | Budig et al. |
| 2010/0063467 A1 | 3/2010 | Addison et al. |
| 2010/0106106 A1 | 4/2010 | Heaton et al. |
| 2010/0106118 A1 | 4/2010 | Heaton et al. |
| 2010/0125259 A1 | 5/2010 | Olson |
| 2010/0159192 A1 | 6/2010 | Cotton |
| 2010/0185163 A1 | 7/2010 | Heagle |
| 2010/0226824 A1 | 9/2010 | Ophir et al. |
| 2010/0262090 A1 | 10/2010 | Riesinger |
| 2010/0267302 A1 | 10/2010 | Kantner et al. |
| 2010/0305490 A1 | 12/2010 | Coulthard et al. |

(56) References Cited

U.S. PATENT DOCUMENTS

| | | |
|---|---|---|
| 2010/0305524 A1 | 12/2010 | Vess et al. |
| 2010/0324516 A1 | 12/2010 | Braga et al. |
| 2011/0046585 A1 | 2/2011 | Weston |
| 2011/0137271 A1 | 6/2011 | Andresen et al. |
| 2011/0160686 A1 | 6/2011 | Ueda et al. |
| 2011/0171480 A1 | 7/2011 | Mori et al. |
| 2011/0172617 A1 | 7/2011 | Riesinger |
| 2011/0224631 A1 | 9/2011 | Simmons et al. |
| 2011/0229688 A1 | 9/2011 | Cotton |
| 2011/0244010 A1 | 10/2011 | Doshi |
| 2011/0257617 A1 | 10/2011 | Franklin |
| 2012/0016322 A1 | 1/2012 | Coulthard et al. |
| 2012/0123359 A1 | 5/2012 | Reed |
| 2012/0143157 A1 | 6/2012 | Riesinger |
| 2012/0258271 A1 | 10/2012 | Maughan |
| 2013/0030394 A1 | 1/2013 | Locke et al. |
| 2013/0066285 A1 | 3/2013 | Locke et al. |
| 2013/0096518 A1 | 4/2013 | Hall et al. |
| 2013/0152945 A1 | 6/2013 | Locke et al. |
| 2014/0039423 A1 | 2/2014 | Riesinger |
| 2014/0039424 A1 | 2/2014 | Locke |
| 2014/0155849 A1 | 6/2014 | Heaton et al. |
| 2014/0171851 A1 | 6/2014 | Addison |
| 2014/0309574 A1 | 10/2014 | Cotton |
| 2014/0350494 A1 | 11/2014 | Hartwell et al. |
| 2015/0030848 A1 | 1/2015 | Goubard |
| 2015/0119830 A1 | 4/2015 | Luckemeyer et al. |
| 2015/0190286 A1 | 7/2015 | Allen et al. |
| 2016/0067107 A1 | 3/2016 | Cotton |

FOREIGN PATENT DOCUMENTS

| | | | |
|---|---|---|---|
| AU | 755496 B2 | 12/2002 | |
| AU | 2009200608 A1 | 10/2009 | |
| CA | 2005436 A1 | 6/1990 | |
| CN | 87101823 A | 8/1988 | |
| DE | 26 40 413 A1 | 3/1978 | |
| DE | 43 06 478 A1 | 9/1994 | |
| DE | 29 504 378 U1 | 9/1995 | |
| DE | 202004018245 U1 | 7/2005 | |
| EP | 0097517 A1 | 1/1984 | |
| EP | 0100148 A1 | 2/1984 | |
| EP | 0117632 A2 | 9/1984 | |
| EP | 0161865 A2 | 11/1985 | |
| EP | 0251810 * | 3/1987 | ............. A61L 15/01 |
| EP | 0251810 A2 | 1/1988 | |
| EP | 0275353 A2 | 7/1988 | |
| EP | 0358302 A2 | 3/1990 | |
| EP | 0538917 A1 | 4/1993 | |
| EP | 0630629 A1 | 12/1994 | |
| EP | 0659390 A2 | 6/1995 | |
| EP | 0633758 B1 | 10/1996 | |
| EP | 1002846 A1 | 5/2000 | |
| EP | 1018967 A1 | 7/2000 | |
| EP | 2578193 A1 | 4/2013 | |
| GB | 692578 A | 6/1953 | |
| GB | 1386800 A | 3/1975 | |
| GB | 2 195 255 A | 4/1988 | |
| GB | 2 197 789 A | 6/1988 | |
| GB | 2 220 357 A | 1/1990 | |
| GB | 2 235 877 A | 3/1991 | |
| GB | 2 329 127 A | 3/1999 | |
| GB | 2 333 965 A | 8/1999 | |
| GB | 2377939 A | 1/2003 | |
| GB | 2392836 A | 3/2004 | |
| GB | 2393655 A | 4/2004 | |
| GB | 2425487 A | 11/2006 | |
| GB | 2452720 A | 3/2009 | |
| GB | 2496310 A | 5/2013 | |
| JP | 1961003393 | 2/1961 | |
| JP | S62139523 U | 9/1987 | |
| JP | S62-275456 A | 11/1987 | |
| JP | 2007254515 A | 10/2007 | |
| JP | 2008080137 A | 4/2008 | |
| JP | 4129536 B2 | 8/2008 | |
| SG | 71559 | 4/2002 | |
| WO | 80/02182 A1 | 10/1980 | |
| WO | 87/04626 A1 | 8/1987 | |
| WO | 8707164 A1 | 12/1987 | |
| WO | 90/010424 A1 | 9/1990 | |
| WO | 93/009727 A1 | 5/1993 | |
| WO | 94/020041 A1 | 9/1994 | |
| WO | 96/05873 A1 | 2/1996 | |
| WO | 9622753 A1 | 8/1996 | |
| WO | 97/18007 A1 | 5/1997 | |
| WO | 99/13793 A1 | 3/1999 | |
| WO | 99/65542 A1 | 12/1999 | |
| WO | 01/36188 A1 | 5/2001 | |
| WO | 01/60296 A1 | 8/2001 | |
| WO | 0168021 A1 | 9/2001 | |
| WO | 0185248 A1 | 11/2001 | |
| WO | 0243743 A1 | 6/2002 | |
| WO | 02062403 A1 | 8/2002 | |
| WO | 03-018098 A2 | 3/2003 | |
| WO | 03045294 A1 | 6/2003 | |
| WO | 03045492 A1 | 6/2003 | |
| WO | 03053484 A1 | 7/2003 | |
| WO | 2004024197 A1 | 3/2004 | |
| WO | 2004037334 A1 | 5/2004 | |
| WO | 2004112852 A1 | 12/2004 | |
| WO | 2005002483 A2 | 1/2005 | |
| WO | 2005062896 A2 | 7/2005 | |
| WO | 2005105176 A1 | 11/2005 | |
| WO | 2005123170 A1 | 12/2005 | |
| WO | 2007022097 A2 | 2/2007 | |
| WO | 2007030601 A2 | 3/2007 | |
| WO | 2007070269 A1 | 6/2007 | |
| WO | 2007085396 A1 | 8/2007 | |
| WO | 2007087811 A1 | 8/2007 | |
| WO | 2007113597 A2 | 10/2007 | |
| WO | 2007133618 A2 | 11/2007 | |
| WO | 2008041926 A1 | 4/2008 | |
| WO | 2008054312 A1 | 5/2008 | |
| WO | 2008/082444 A2 | 7/2008 | |
| WO | 2008/100440 A2 | 8/2008 | |
| WO | 2008104609 A1 | 9/2008 | |
| WO | 2008/131895 A1 | 11/2008 | |
| WO | 2009/002260 A1 | 12/2008 | |
| WO | 2008149107 A1 | 12/2008 | |
| WO | 2009066105 A1 | 5/2009 | |
| WO | 2009066106 A1 | 5/2009 | |
| WO | 2009081134 A1 | 7/2009 | |
| WO | 2009089016 A1 | 7/2009 | |
| WO | 2009/124100 A1 | 10/2009 | |
| WO | 2009126103 A1 | 10/2009 | |
| WO | 2010032728 A1 | 3/2010 | |
| WO | 2010/056977 A2 | 5/2010 | |
| WO | 2010129299 A2 | 11/2010 | |
| WO | 2011008497 A2 | 1/2011 | |
| WO | 2011/049562 A1 | 4/2011 | |
| WO | 2011043786 A1 | 4/2011 | |
| WO | 2011115908 A1 | 9/2011 | |
| WO | 2011121127 A1 | 10/2011 | |
| WO | 2011162862 A1 | 12/2011 | |
| WO | 2012/112204 A1 | 8/2012 | |
| WO | 2012104584 A1 | 8/2012 | |
| WO | 2012140378 A1 | 10/2012 | |
| WO | 2012143665 A1 | 10/2012 | |
| WO | 2013009239 A1 | 1/2013 | |
| WO | 2013090810 A1 | 6/2013 | |
| WO | 2014039557 A1 | 3/2014 | |
| WO | 2014/113253 A1 | 7/2014 | |
| WO | 2014140608 A1 | 9/2014 | |
| WO | 2014143488 A1 | 9/2014 | |
| WO | 2015/065615 A1 | 5/2015 | |
| WO | 2015130471 A1 | 9/2015 | |

OTHER PUBLICATIONS

R. White, "Evidence for atraumatic soft silicone wound dressing use". Wound, UK (2005), vol. 3, pp. 104-108, Mepilex Border docs, (2001).

(56) References Cited

OTHER PUBLICATIONS

European Search Report for corresponding application 17183683.6, dated Sep. 18, 2017.
European Search Report for corresponding application 17164033.7, dated Oct. 13, 2017.
Extended European Search Report for corresponding application 17191970.7, dated Oct. 26, 2017.
NPD 1000 Negative Pressure Would Therapy System, Kalypto Medical, pp. 1-4, dated Sep. 2008.
European Search Report for corresponding EP Application 171572787 dated Jun. 6, 2017.
International Search Report and Written Opinion for corresponding application PCT/US2016/031397, dated Aug. 8, 2016.
European Search Report for corresponding application 17167872.5, dated Aug. 14, 2017.
European Examination Report dated Jun. 29, 2016, corresponding to EP Application No. 16173614.5.
European Search Report for corresponding EPSN 15157408.4 published on Sep. 30, 2015.
International Search Report and Written Opinion for PCT/GB2008/003075 dated Mar. 11, 2010.
International Search Report and Written Opinion for PCT/GB2008/004216 dated Jul. 2, 2009.
International Search Report and Written Opinion for PCT/GB2012/000099 dated May 2, 2012.
EP Examination Report for corresponding application 12705381.7, dated May 22, 2014.
International Search Report and Written Opinion for PCT/US2012/069893 dated Apr. 8, 2013.
International Search Report and Written Opinion for PCT/US2013/070070 dated Jan. 29, 2014.
International Search Report and Written Opinion for PCT/US2014/016320 dated Apr. 15, 2014.
International Search Report and Written Opinion for PCT/US2014/056566 dated Dec. 5, 2014.
International Search Report and Written Opinion for PCT/US2014/056508 dated Dec. 9, 2014.
International Search Report and Written Opinion for PCT/US2014/056524 dated Dec. 11, 2014.
International Search Report and Written Opinion for PCT/US2014/056594 dated Dec. 2, 2014.
Partial Internationl Search Report dated Jul. 31, 2009; PCT Internationl Application No. PCT/US2009/036222.
International Search Report and Written opinion dated Dec. 15, 2009; PCT Internation Application No. PCT/US2009/036222.
International Search Report and Written Opinion dated Feb. 24, 2010; PCT/US2009/057182.
International Search Report and Written Opinion dated Jan. 5, 2010; PCT International Application No. PCT/US2009/057130.
Response filed Oct. 20, 2011 for U.S. Appl. No. 12/398,904.
Interview Summary dated Oct. 27, 2011 for U.S. Appl. No. 12/398,904.
Non-Final Office Action dated Jul. 20, 2011 for U.S. Appl. No. 12/398,904.
NDP 1000 Negative Pressure Wound Terapy System, Kalypto Medical, pp. 1-4.
Partial International Search Report dated Jul. 31, 2009 for PCT International Application No. PCT/US2009/036217.
International Search Report and Written Opinion dated May 31, 2010 for PCT Application No. PCT/US2009/064364.
Examination report for AU2009221772 dated Apr. 4, 2013.
Response filed Oct. 21, 2011 for U.S. Appl. No. 12/398,891.
Interview Summary dated Oct. 27, 2011 for U.S. Appl. No. 12/398,891.
Restriction Requirement dated Jun. 13, 2011 for U.S. Appl. No. 12/398,891.
Response filed Jun. 24, 2011 for U.S. Appl. No. 12/398,891.
Non-Final Office Action dated Jul. 21, 2011 for U.S. Appl. No. 12/398,891.
Partial International Search Report date dated Jul. 31, 2009 for PCT International Application No. PCT/US2009/036211.

International Search Report and Written Opinion dated Oct. 19, 2010; PCT International Application No. PCT/US2009/036217.
International Search Report and Written Opinion dated Feb. 24, 2010; PCT International Application No. PCT/US2009/057182.
NPD 1000 Negative Pressure Would Therapy System, Kalypto Medical, pp. 1-4.
Partial International Search Report dated Jul. 31, 2009; PCT Internationl Application No. PCT/US2009/036222.
Non-Final Rejection for U.S. Appl. No. 12/398,904 dated Mar. 14, 2012.
Response to Non-Final Rejection for U.S. Appl. No. 12/398,904 filed Jun. 4, 2012.
International Search Report and Written Opinion for PCT/US2014/061251 dated May 8, 2015.
International Search Report and Written Opinion for PCT/IB2013/060862 dated Jun. 26, 2014.
International Search Report and Written Opinion for PCT/US2015/015493 dated May 4, 2015.
European Search Report for corresponding Application No. 15194949.2.
International Search Report and Written Opinion for PCT/US2015/034289 dated Aug. 21, 2015.
International Search Report and Written Opinion for PCT/US2015/065135 dated Apr. 4, 2016.
International Search Report and Written Opinion for PCT/GB2012/050822 dated Aug. 8, 2012.
International Search Report and Written Opinion for PCT/US2015/029037 dated Sep. 4, 2015.
International Search Report and Written Opinion dated Jun. 1, 2011 for PCT International Application No. PCT/US2011/028344.
European Search Report for EP 11714148.1, dated May 2, 2014.
European Search Report for corresponding Application No. 15192606.0 dated Feb. 24, 2016.
International Search Report and Written Opinion for corresponding PCT/US2014/048081 dated Nov. 14, 2014.
International Search Report and Written Opinion for corresponding PCT/US2014/010704 dated Mar. 25, 2014.
Louis C. Argenta, MD and Michael J. Morykwas, PHD; Vacuum-Assisted Closure: A New Method for Wound Control and Treatment: Clinical Experience; Annals of Plastic Surgery.
Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 198, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.

(56) References Cited

OTHER PUBLICATIONS

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians; Jul. 2007.
International Search Report and Written Opinion for corresponding PCT application PCT/US2016/051768 dated Dec. 15, 2016.

* cited by examiner

PATTERNED SILICONE COATING

This application is a divisional of U.S. Non-Provisional patent application Ser. No. 14/111,626, filed Jan. 23, 2014, which claims the priority benefit of PCT/GB2012/050822, filed Apr. 13, 2012, which claims the benefit of GB 1106491.2, filed Apr. 15, 2011, all of which are incorporated herein by reference for all purposes.

The present invention relates to methods of providing patterned coatings of silicone adhesives on sheet-like substrates, in particular on medical substrates such as wound dressings.

Silicone pressure-sensitive adhesives are known for use in medical products such as wound dressings. The silicone adhesives have high medical acceptability and are capable of being sterilized by conventional methods such as autoclaving, gamma and ethylene oxide without loss of properties. A drawback of the silicone adhesives is that they have limited oxygen and moisture permeability. This means that a continuous coating of the silicone adhesive on, for example, a wound dressing backing sheet, results in poor breathability of the resulting wound dressing. It is therefore desirable to provide a discontinuous silicone adhesive layer to maintain breathability of the dressing.

Soft silicone adhesives are prepared from a fluid polymerizable precursor mixture that is coated onto a substrate, for example by dip-coating or coating process, followed by thermal curing. The precursor composition is desirably a solventless composition. The resulting soft silicone adhesives are generally soft and tacky, but generally solvent free, and therefore readily repositionable on the skin.

Hitherto, discontinuous silicone adhesive layers have been provided by coating the silicone adhesive precursor onto an open mesh substrate, such as a gauze, so that the apertures of the substrate remain open after coating with the precursor, followed by curing of the coated substrate. The resulting silicone adhesive-coated, open mesh structure can then be applied to a suitable substrate such as a semipermeable wound dressing backing sheet. Coated mesh silicone adhesive structures of this type are described, for example, in EP-A-0251810.

US-A-20050233072 describes a method of applying a pattern coating of hydrogel forming polymer onto a substrate, comprising moving the substrate through a slot coater that applies a patterned coating of a low-viscosity polymerizable and/or crosslinkable polymer precursor material to the substrate, followed by polymerizing the coating downstream of the coater.

However, it has not previously been suggested to pattern coat a silicone adhesive directly onto a substrate such as a backing sheet. This may be because the silicone adhesive precursor is viscous and solvent-free, and therefore cannot be used in conventional pattern coating methods such as screen printing or slot coating. Furthermore, silicone compositions are generally incompatible with common hydrophilic wound dressing materials, whereby they adhere relatively weakly to such materials unless a primer coating is applied between the substrate and the silicone adhesive. This further hinders conventional pattern coating with silicone adhesives.

In a first aspect, the present invention provides a method of applying a patterned coating of a silicone adhesive to a substrate sheet, comprising the steps of pattern coating a silicone precursor composition onto the substrate, followed by thermally curing the precursor composition coated on the substrate.

In a first embodiment, the step of pattern coating is performed by the steps of coating the silicone prepolymer composition onto an apertured support layer having holes and lands to provide a coated apertured support layer, followed by applying the coated support layer to the substrate sheet, followed by removing the coated apertured support layer to leave a patterned layer of the silicone composition on the substrate sheet. This method results in a pattern of the silicone on the substrate sheet that substantially corresponds to the pattern of lands on the support layer. The support layer may be removed before or after the step of curing the silicone.

In a second embodiment, the step of pattern coating is performed by providing a mold having a base surface and recesses in said surface corresponding to the desired adhesive pattern, filling said recesses with said silicone prepolymer composition, applying said substrate sheet to said base surface so that it contacts the prepolymer mixture in the recesses, curing said prepolymer mixture in contact with the substrate sheet, and removing the substrate sheet and silicone layer from the mold. In other words, this embodiment covers various forms intaglio printing of the silicone prepolymer onto the substrate. The pattern of recesses can be connected to form a connected layer of the silicone with apertures, or the recesses may be separated from each other on the surface of the mold so that separate areas of silicone are deposited on the support sheet. The process may be carried out in discontinous fashion using a plurality of flat molds, or in continuous fashion using an intaglio roller.

In a third embodiment, the method comprises providing a mold sheet having upper and lower surfaces and a patter of apertures extending between the upper and lower surfaces, filling the apertures with the fluid silicone prepolymer composition, contacting one of said upper or lower surfaces with the support sheet so that said support sheet contacts said fluid silicone prepolymer composition in said apertures, curing the silicone prepolymer composition in contact with the support sheet, and removing the mold sheet. The step of curing may be carried out before or after the step of curing. This method resembles screen printing, but the apertures in the mold sheet are substantially larger than the apertures conventionally used for printing screens so that the viscosity of the silicone precursor does not hinder printing. The process may be carried out in discontinous fashion using a plurality of flat mold sheets, or in continuous fashion using an apertured roller as described in more detail below.

The invention will now be described in more detail with reference to the accompanying drawings, in which.

Figure 1:
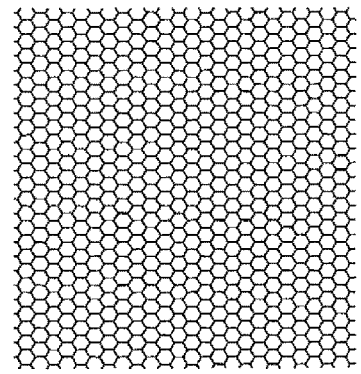
FIG. 1 shows a mesh suitable for use as a support layer in the block printing embodiments according to the present invention.

As noted above, in a first aspect the present invention provides a method of applying a patterned coating of a silicone adhesive to a substrate sheet, comprising the steps of pattern coating a silicone precursor composition onto the substrate, followed by curing the precursor composition coated on the substrate.

The pattern of silicone adhesive may be any regular or irregular pattern. In certain embodiments the pattern has translational symmetry along at least one axis, for example along two or three axes. In certain embodiments, the pattern is in the form of a network of adhesive coating, such as a mesh pattern or a honeycomb pattern. In other embodiments the pattern consist of a plurality of islands, dots, or patches of adhesive separated by adhesive-free regions of the substrate. In yet other embodiments, the pattern may be in the form of an adhesive-coated margin or annulus surrounding an adhesive-free area, for example for the production of adhesive-bordered dressings. In any event, the adhesive pattern suitably covers from about 10% to about 90% of the area of the coated surface of the substrate, for example from about 20% to about 50% of said area. The patterning of the adhesive is macroscopic, for example the minimum width dimension of any coated area is suitably greater than about 2 mm. The density of the coating is suitably from about 20 gsm to 350 gsm, more suitably from about 30 gsm to about 250 gsm.

The substrate sheet suitably provides a protective covering, cushioning, mechanical support and/or liquid absorbency, for example in a wound dressing. Suitably, the substrate sheet is formed from a material that is hydrophilic, suitably a material that does not swell or dissolve significantly in water or wound fluid. Suitably, the substrate sheet has an uncompressed thickness of from about 0.2 mm to about 15 mm, for example from about 0.5 mm to about 5 mm.

The substrate sheet may be any of the layers conventionally used to form layers over a wound contacting layer in a laminated wound dressing, for example absorbent layers or backing layers. In certain embodiments, the substrate sheet is a backing layer in the form of a sheet of continuous semipermeable or impermeable polymer. In other embodiments the substrate sheet may be an absorbent layer for example a hydrophilic foam, a sponge, a film, or a textile layer. The textile may be nonwoven, knitted or woven.

The curing of the silicone prepolymer in situ achieves strong bonding between the silicone adhesive and substrate sheet surfaces that are normally incompatible with and non-adherent to silicone, including hydrophilic surfaces such as polyurethane or hydrocolloid surfaces. This bonding is suitably achieved without the use of a silicone primer to improve adhesion, i.e. it is direct bonding between the silicone and the material of the substrate sheet.

In particular embodiments, the substrate sheet is (a) a semipermeable or impermeable polymer film, or (b) a hydrophilic foam sheet, or (c) a nonwoven web.

Suitable semipermeable or impermeable polymer films for the substrate sheet include any of the semipermeable films conventionally used to form a backing sheet of wound dressings. The films are suitably continuous, i.e. they do not comprise macroscopic apertures that would allow passage of wound fluid. Suitably, the substrate sheet in these embodiments is also microorganism-impermeable. Suitable continuous conformable substrate sheets of this type will suitably have a moisture vapor transmission rate (MVTR) of the substrate sheet alone of 300 to 35000 $g/m^2/24$ hrs, suitably 500 to 25000 $g/m^2/24$ hrs at 37.5° C. at 100% to 10% relative humidity difference (measured before coating with the silicone adhesive). It has been found that such moisture vapor transmission rates allow the wound under the dressing to heal under moist conditions without causing the skin surrounding the wound to macerate. The substrate sheet thickness in these embodiments is suitably in the range of 10 to 1000 micrometers, more suitably 100 to 500 micrometers.

Suitable polymers for forming the substrate sheet in these embodiments include polyurethanes and poly alkoxyalkyl acrylates and methacrylates. Suitably, the substrate sheet in these embodiments comprises a continuous layer of a high density blocked polyurethane foam that is predominantly closed-cell. A suitable backing sheet material is the polyurethane film available under the Registered Trade Mark ESTANE 5714F. Also suitable are elastomeric polymeric esters such as Du Pont HYTREL (Registered Trade Mark).

Suitable hydrophilic foam sheets for use as the substrate sheet include polyurethane foams, carboxylated butadiene-styrene rubber, polyacrylate, polyvinylic or cellulosic foams. The hydrophilic foam may be open-cell or closed-cell. Suitably, the foam comprises a polyurethane, and more suitably it comprises at least 50% by weight of one or more polyurethanes, for example at least 75% by weight thereof.

The hydrophilic polyurethane foam materials are formed by reacting particular diisocyanates or isocyanate-capped prepolymers with suitable chain extending compounds having amine and/or alcohol multiple functionality. Chain terminating compounds such as mono-amines or monohydric alcohols may be included in the reaction mixture. Water may be included in the reaction mixture, since it reacts with isocyanate to liberate carbon dioxide for foaming the mixture.

The hydrophilic foams used in the substrate sheets of the invention may also have the property of swelling and expanding when water is absorbed. The degree of swelling of the hydrophilic foams on complete saturation with an aqueous medium is typically at least 100% (expressed in terms of increase in volume), and suitably at least 200%. Preferred foams swell by 400 to 800%. Despite this high degree of swelling, however, the foams of the invention retain their integrity even after absorption of large quantities of water. Typically, the cells of the hydrophilic foams have an average diameter in the range 0.1 to 0.6 mm. Suitably hydrophilic foams are as described in EP-A-0541391. These foam layers are available from Systagenix Wound Management under the Registered Trade Marks TIELLE and HYPOL.

Suitably, the basis weight of the hydrophilic foam when used as a substrate sheet in the materials of the present invention is from 0.2 to 1.5 $kg/m^2$, more suitably 0.5 to 1.0 $kg/m^2$.

Suitable textiles for use as the substrate sheet include any of those conventionally used for absorbent products, including cellulose woven or nonwoven webs, or cellulose derivatives such as viscose, rayon or oxidized regenerated cellulose. In certain embodiments, the fabric comprises at least about 10 wt. % of hydrogel-forming absorbent fibers based on the dry weight of the fabric, for example, the fabric comprises at least about 20 wt. % of the hydrogel-forming fibers, for example from about 30 wt. % to about 50 wt. % of such fibers.

The term "hydrogel-forming fibers" refers to fibers that can absorb at least about twice their own weight of water, suitably at least about four times their own weight of water, to form a hydrogel. The fibers are normally insoluble in water. Suitable materials for the hydrogel-forming fibers include alginates, carboxymethylcelluloses, hydroxyethylcelluloses, polyacrylates, and hyaluronates. Suitable materials are calcium alginate and sodium carboxymethylcellulose and mixtures thereof.

Suitably, the fabric comprises at least about 10 wt. % based on the dry weight of the fabric of substantially non-water-absorbent textile fibers, and suitably it comprises at least about 20 wt. % of such fibers, for example from about 30 wt. % to about 60 wt. % of such fibers. Suitable non-absorbent textile fibers include polyamide fibers such as nylon fibers, polyolefin fibers, and viscose fibers.

In some embodiments, the absorbent layer is similar to those described in WO03/053584. That is to say, the absorbent layer comprises or consists essentially of a nonwoven fabric made up of a mixture of from about 10 wt. % to about 90 wt. % of hydrogel-forming absorbent fibers and from about 90 wt. % to about 10 wt. % of non-absorbent textile fibers. In certain embodiments, at least some of the non-absorbent textile fibers are coated with metallic silver ($Ag^0$) as an antimicrobial agent. Suitably, the amount of silver in the fabric is from about 0.1% to about 10 wt. %, based on the dry weight of the fabric. Textiles of this kind are available from Systagenix Wound Management under the Registered Trade Mark SILVERCEL.

The basis weight of the textile substrate sheet may be in the range of 50-500 g/m$^2$, such as 100-400 g/m$^2$. The uncompressed thickness of the textile layer may be in the range of from 0.5 mm to 10 mm, such as 1 mm to 4 mm. The free (uncompressed) liquid absorbency measured for physiological saline may be in the range of 5 to 30 g/g at 25° C.

Suitably, the silicone precursor composition is substantially or completely solvent-free. For example, the precursor composition may comprise less than about 10 wt. % of solvent, typically less than about 1 wt. % of solvent. The term "solvent" is used in its usual sense, that is to say organic and/or aqueous liquid solvents or diluents that do not form part of the final adhesive polymer composition. Suitably, the precursor composition is a viscous fluid, for example a fluid having a viscosity of at least about 1 Pa s, typically about 2 Pa s to about 20 Pa s at 20° C.

Suitably, the silicone composition is a so-called soft skin adhesive silicone elastomer. Such silicones can be made by an addition reaction (hydrosilylation) between (a) a vinyl functional polydimethyl siloxane, such as bis-dimethyl vinyl PDMS, and (b) a hydrogen functional siloxane, such as dimethyl, methylhydrogen siloxane copolymers, hydrogen dimethylsiloxy terminated PDMS. The cure reaction is catalyzed by a hydrosilylation catalyst, such as a noble metal catalyst, suitably a platinum catalyst. Suitably the silicone prepolymer composition further comprises a polymerization inhibitor that is evaporated from said composition during said step of thermally partially curing, for example 2-methyl-3-butyn-2-ol. The polymerization inhibitor is suitably present in an amount of from about 0.001 wt. % to about 1 wt. %, for example from about 0.01 wt. % to about 0.1 wt. % before curing.

Silicone skin adhesive compositions are suitably supplied as two-part systems: Part A contains at least the vinyl prepolymer and the catalyst, while Part B contains the vinyl prepolymer and the SiH siloxane cross linker. The components are mixed immediately before use, optionally with addition of the polymerization inhibitor, to form the adhesive precursor composition.

In embodiments, the silicone coating composition comprises or consists essentially of the following components:

(A) a diorganopolysiloxane having at least 2 alkenyl groups in each molecule;

(B) an organohydrogenpolysiloxane having at least 2 silicon-bonded hydrogen atoms in each molecule, in a quantity sufficient for the ratio between the number of moles of silicon-bonded hydrogen atoms in this component and the number of moles of alkenyl groups in component (A) to have a value of from about 0.6:1 to about 20:1, (C) optionally a platinum group metal catalyst suitably in a quantity providing 0.1 to 500 weight parts as platinum group metal per 1,000,000 weight parts component (A); and (D) a volatile polymerization inhibitor, suitably selected from: alkyne alcohols such as 2-methyl-3-butyn-2-ol, 3,5-dimethyl-1-hexyn-3-ol, and phenylbutynol; ene-yne compounds such as 3-methyl-3-penten-1-yne and 3,5-dimethyl-3-hexen-1-yne; tetramethyltetrahexenyl-cyclotetrasiloxane; and benzotriazole.

The diorganopolysiloxane, component (A), used in the instant invention is the base component of the total composition. This diorganopolysiloxane must contain at least 2 alkenyl groups in each molecule in order for this composition to cure into a rubbery elastic silicone rubber coating composition.

The diorganopolysiloxane (A) comprises essentially straight-chain organopolysiloxane with the average unit formula $R_nSiO_{(4-n)/2}$, wherein R is selected from substituted and unsubstituted monovalent hydrocarbon groups and n has a value of 1.9 to 2.1. R may be exemplified by alkyl groups such as methyl, ethyl, propyl, and others; alkenyl groups such as vinyl, allyl, and others; aryl groups such as phenyl, and others; and haloalkyl groups such as 3,3,3-trifluoropropyl and others. The diorganopolysiloxane (A) should have a viscosity at 25° C. of at least 100 centipoise (1 dPa·s). When such factors as the strength of the silicone rubber coating membrane, and blendability are taken into account, the viscosity of diorganopolysiloxane (A) at 25° C. is preferably from 1,000 centipoise (1 Pa·s) to 100,000 centipoise (100 Pa·s). The diorganopolysiloxane (A) may be exemplified by dimethylvinylsiloxy-endblocked dimethylpolysiloxanes, dimethylvinylsiloxy-endblocked dimethylsiloxane-methylvinylsiloxane copolymers, and dimethylvinyl-siloxy-endblocked dimethylsiloxane-methylphenylsiloxane copolymers.

Component (B), an organopolysiloxane that contains at least 2 silicon-bonded hydrogen atoms in each molecule, is a crosslinker for the composition of the instant invention. The organopolysiloxane (B) may be exemplified by trimethylsiloxy-endblocked methylhydrogenpolysiloxanes, trimethylsiloxy-endblocked dimethylsiloxanemethylhydrogen-siloxane copolymers, dimethylphenylsiloxy-endblocked methylphenylsiloxanemethyl-hydrogensiloxane copolymers, cyclic methylhydrogenpolysiloxanes, and copolymers that contain the dimethylhydrogensiloxy unit and SiO4/2 unit. The organohydrogenpolysiloxane (B) should be added in a quantity that the ratio between the number of moles of silicon-bonded hydrogen atoms in this organohydrogenpolysiloxane and the number of moles of alkenyl groups in component (A) has a value of 0.6:1 to 20:1.

The platinum group metal catalyst, component (C), used in the compositions is a curing catalyst. The platinum group metal catalyst (C) may be exemplified by platinum micropowder, platinum black, chloroplatinic acid, platinum tetrachloride, olefin complexes of chloroplatinic acid, alcohol solutions of chloroplatinic acid, complexes between chloroplatinic acid and alkenylsiloxanes, rhodium compounds, and palladium compounds. The platinum group metal catalyst (C) should be added generally at 0.1 to 500 weight parts as platinum group metal per 1,000,000 weight parts component (A), and is preferably used at 1 to 50 weight parts as platinum group metal per 1,000,000 weight parts component (A). The reaction will not develop adequately at less than 0.1 weight parts, while additions in excess of 500 weight parts are uneconomical.

The step of curing the silicone adhesive precursor normally comprises thermal curing to at least partially cure the silicone. The thermal curing is suitably performed continuously by passing the coated substrate through an oven. Suitable thermal curing conditions include exposure to a temperature of from about 80° C. to about 200° C., for example about 120° C. to about 180° C. for a time of from about 1 minute to about 10 minutes, for example about 1.5 minutes to about 5 minutes. Especially suitable conditions are 110°-150° C. for 2 to 6 minutes. The elevated temperature results in evaporation of the polymerization inhibitor (when present) from the silicone composition and therefore in polymerization of the silicone. The resulting material is chemically polymerized and dimensionally stable, but may be capable of further curing by ionizing radiation as explained further below.

The thermally cured material may then be subjected to a final cure with ionizing radiation. The ionizing radiation is suitably selected from e-beam radiation and gamma radiation. A variety of procedures for E-beam and gamma ray curing are well-known. The cure depends on the specific equipment used, and those skilled in the art can define a dose calibration model for the specific equipment, geometry, and line speed, as well as other well understood process parameters. The final cure may form part of the final sterilization by irradiation of the products of the invention. Suitably, the method of the invention further comprises the step of packaging the material in a microorganism-impermeable container prior to the step of further curing with ionizing radiation, whereby the step of further curing also sterilizes the material.

Commercially available electron beam generating equipment is readily available. For example, a Model CB-300 electron beam generating apparatus (available from Energy Sciences, Inc. (Wilmington, Mass.). Generally, a support film (e.g., polyester terephthalate support film) runs through a chamber. Generally, the chamber is flushed with an inert gas, e.g., nitrogen while the samples are e-beam cured. Multiple passes through the e-beam sterilizer may be needed.

Commercially available gamma irradiation equipment includes equipment often used for gamma irradiation sterilization of products for medical applications. Cobalt 60 sources are appropriate. Total absorbed doses are suitably from 20 to 60 kGy, more suitably from about 35 to 50 kGy and dose rates are suitably about 7 to 8 kGy/hour.

The step of further curing with ionizing radiation is also effective to bond the silicone adhesive more strongly to the surface of the substrate layer. This is thought to be due to the ionizing radiation forming covalent bonds between the silicone and the substrate layer material.

The final cured silicone adhesive coating is suitably gel- or elastomer-like, substantially hydrophobic, and moderately adherent (tacky). This coating is therefore suitable for direct application to and removal from wounds without excessive trauma, and/or for repositionable application to skin.

In a first embodiment, the step of pattern coating is performed by the steps of coating the silicone prepolymer composition onto an apertured support layer having holes and lands to provide a coated apertured support layer, followed by applying the coated support layer to the substrate sheet, followed by removing the coated apertured support layer to leave a patterned layer of the silicone composition on the substrate sheet. This method results in a pattern of the silicone on the substrate sheet that substantially corresponds to the pattern of lands on the support layer. Thus, the method resembles block printing in that the coated apertured support layer is used as a printing block to print a pattern of silicone prepolymer onto the substrate.

The support layer may be removed before or after the step of curing the silicone. Suitably, the support layer has a surface that is relatively non-adherent to the silicone adhesive, for example a perfluorocarbon surface.

The support layer may be a mesh or web or fabric suitably formed from a woven, nonwoven or knitted textile, or it may be a molded mesh, or it may be an apertured continuous film. A typical perforated plastic sheet substrate layer is shown in FIG. 1.

The size and shape of the apertures in the support layer generally correspond to the desired adhesive-free areas of the silicone coated substrate. The apertures generally have an aspect ratio of from 1:1 to 5:1, and preferably from 1:1 to 2:1 For example, the apertures may be approximately circular or approximately square. The apertures suitably have an average diameter of from about 2 to about 4 mm, and more suitably from about 3 to about 5 mm. The open area of the support may for example be from about 30% to about 90%, for example from about 50% to about 80%.

The support sheet is suitably formed from any medically acceptable material, such as cellulose, polyolefins, polyesters, or polyamides.

The support sheet is coated with the silicone adhesive prepolymer composition by any suitable means, such as dip-coating or roller coating. Air or another gas may be blown through the coated support to ensure that the apertures are open before applying the coated support to the substrate. The support sheet is suitably then lifted off the substrate to leave a pattern of silicone adhesive prepolymer on the substrate, which is then cured. In other embodiments, the curing is carried out with the support sheet on the substrate, followed by lifting the support sheet off the cured silicone. The latter embodiments require, of course, that the cured silicone adhesive is less adherent to the support than to the substrate.

In a second embodiment, the step of pattern coating is performed by providing a mold having a base surface and recesses in said surface corresponding to the desired adhesive pattern, filling said recesses with said silicone prepolymer composition, applying said substrate sheet to said base surface so that it contacts the prepolymer mixture in the recesses, curing said prepolymer mixture in contact with the substrate sheet, and removing the substrate sheet and silicone layer from the mold. In other words, this embodiment covers various forms intaglio printing of the silicone prepolymer onto the substrate.

The pattern of recesses can be connected to form a connected layer of the silicone with apertures, or the recesses may be separated from each other on the surface of the mold so that separate areas of silicone are deposited on the support sheet. The depth of the recesses is suitably from about 0.1 mm to about 2 mm, for example about 0.2 mm to about 1 mm. The mold is suitably formed from metal or polymer.

The recesses are suitably filled with the silicone prepolymer composition by flooding the mold with the prepolymer composition, followed by wiping with e.g. a doctor blade to remove the prepolymer from the base surface of the mold outside the recesses. Curing of the prepolymer is performed after printing, as described above.

Figure 2:
FIG. 2 shows a flat mold suitable for use in a batch intaglio printing method according to the present invention.

The process may be carried out in discontinous fashion using a plurality of flat molds, or in continuous fashion using an intaglio roller. A suitable flat mold is shown in FIG. 2. The mold 1 is formed of polytetrafluoroethylene, and comprises a flat base surface 2 having recesses 3 formed therein by any suitable method such as injection molding or machining. The recesses 3 in this embodiment have substantially constant depth of about 0.5 mm. The recesses 3 are filled with the silicone prepolymer composition 4 by flooding the mold with the prepolymer composition, followed by wiping the base surface 2 with a doctor blade (not shown) to remove excess prepolymer. Substrate layer 6 is laid on top of the base surface 2, optionally with application of pressure, and is then peeled away to provide the substrate layer having patterned silicone adhesive prepolymer thereon. Curing is then carried out.

Figure 3:
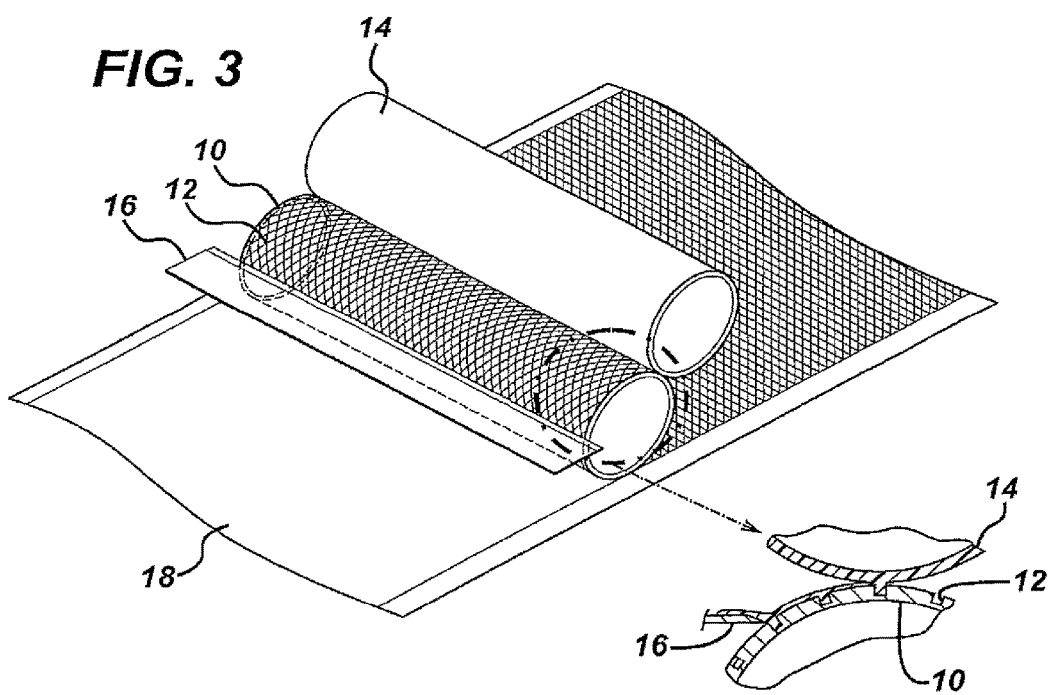
FIG. 3 shows a schematic view of a roller intaglio printing method according to the present invention.
Figure 4:
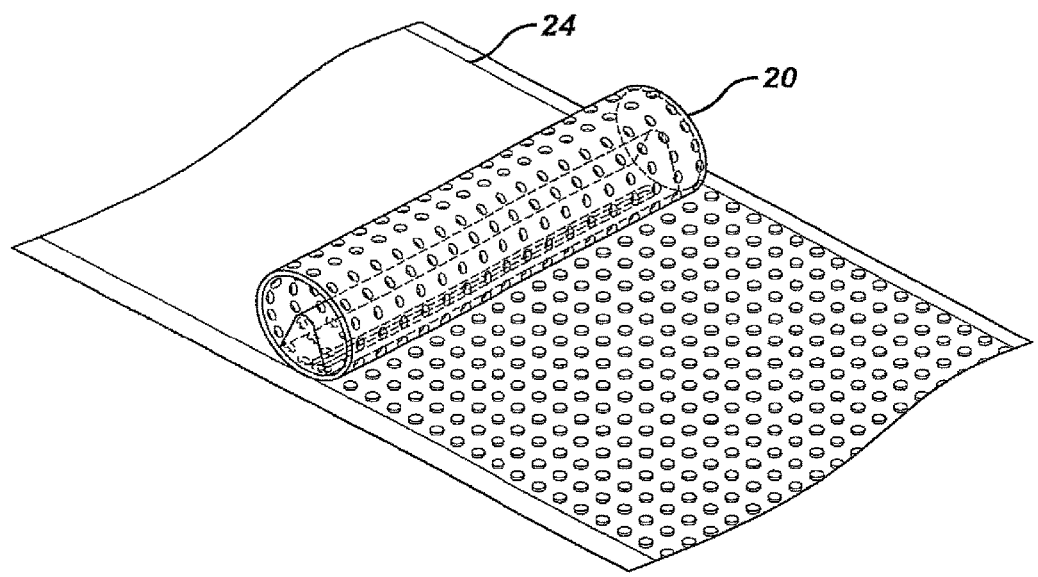
FIG. 4 shows a schematic view of a roller screen printing method according to the present invention.

A suitable roller method is shown in FIG. 3. In these embodiments, the roller 10 is formed having recesses 12 in its outer surface as hereinbefore described. The prepolymer is applied in a continuous layer to the outside surface of the intaglio roller 10 by a transfer roller 14. A doctor blade 16 wipes the outer surface of the intaglio roller leaving the apertures filled with the prepolymer. The coated roller is then applied to the moving substrate 18 to print the prepolymer onto the substrate 18, followed by curing.

In a third embodiment, the method of the present invention comprises providing a mold sheet having upper and lower surfaces and a pattern of apertures extending between the upper and lower surfaces, filling the apertures with the fluid silicone prepolymer composition, contacting one of said upper or lower surfaces with the support sheet so that said support sheet contacts said fluid silicone prepolymer composition in said apertures, curing the silicone prepolymer composition in contact with the support sheet, and removing the mold sheet. The step of curing may be carried out before or after the step of removing the mold sheet.

This method resembles screen printing, but the apertures in the mold sheet are substantially larger than the apertures in conventional printing screens so that the viscosity of the silicone precursor does not hinder printing. Suitably, the thickness of the mold sheet is from about 0.1 mm to about 2 mm, for example from about 0.2 mm to about 1 mm. The mold sheet may for example be a perforated metal sheet, a perforated plastic sheet, or a textile sheet having large apertures. The open area of the mold sheet is suitably from about 10% to about 90% of the total area, for example from about 10% to about 50% of the total area of the mold sheet.

Suitably, the apertures in the mold sheet are filled with the silicone adhesive prepolymer composition by flooding the mold sheet with prepolymer, followed by wiping excess prepolymer from the surfaces of the mold sheet, for example with a doctor blade. The step of flooding the mold sheet with prepolymer is suitably performed while one of the surfaces of the mold sheet is in contact with the substrate sheet.

Figure 5:
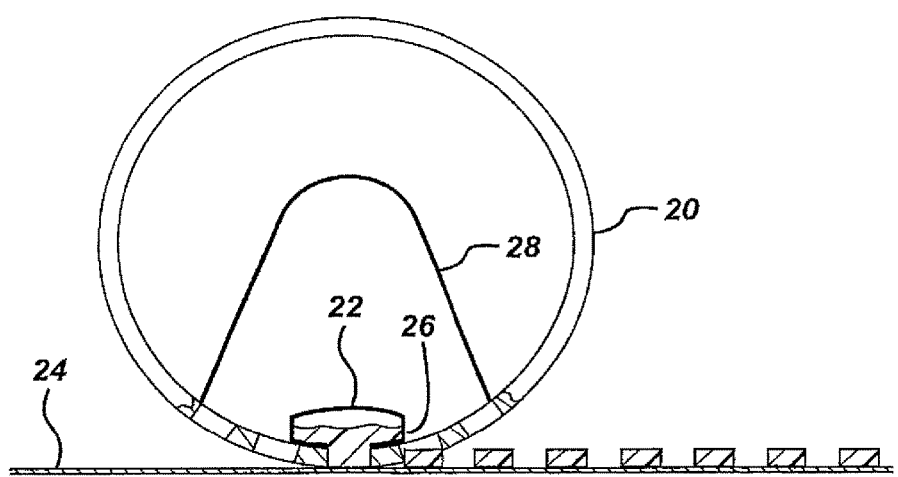
FIG. 5 shows a cross-section through the roller of FIG. 4.

The process may be carried out in discontinuous fashion using a plurality of flat mold sheets, or in continuous fashion using an apertured roller. A suitable roller method is shown in FIG. 5. In these embodiments, the screen printing roller 20 is formed from a mold sheet material as hereinbefore described. The prepolymer is pumped into channel 22 inside the roller so that it is fed selectively to the apertures of the roller 20 that are in contact with the substrate sheet 24. The position of the channel 22 is fixed as the roller rotates, so that one edge 26 of the channel acts as a doctor blade to wipe the inside surface of the roller after the apertures have been filled with the prepolymer. A concentric channel 28 may be provided that is fed with compressed air (or other compressed gas) to ensure that the prepolymer in the apertures is transferred to the substrate sheet 24 as the roller rotates. The printed substrate sheet is then cured.

In a second aspect, the present invention provides a substrate sheet having a patterned silicone adhesive coating thereon, obtainable by a method according to the present invention.

Figure 6:
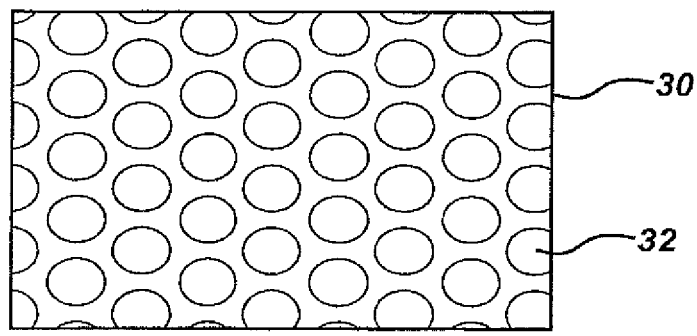
FIG. 6 shows a perspective view of a silicone-adhesive pattern coated substrate according to the present invention.

FIG. 6 shows a printed substrate sheet according to this aspect of the invention. The substrate 30 is a semipermeable polyurethane wound dressing backing sheet. The patterned silicone adhesive 32 is in the form of an open network of adhesive formed by block printing a mesh coated with the silicone prepolymer onto the substrate followed by curing. In other embodiments, the adhesive may be patterned as a continuous adhesive margin extending around the perimeter of the substrate sheet, whereby the central region of the substrate sheet is adhesive-free. The width of the adhesive coated margin is suitably from about 1 cm to about 4 cm. The adhesive-coated margin can then be used to attach the substrate sheet to skin surrounding a wound.

In a further aspect, the present invention provides a wound dressing comprising a substrate sheet according to the second aspect of the invention.

Suitably, the wound dressing according to the present invention is in the form of a piece having a total area of from about 1 cm$^2$ to about 1000 cm$^2$, for example from about 5 cm$^2$ to about 400 cm$^2$.

The dressing may comprise one or more releasable cover sheets over the adhesive pattern coated surface of the substrate to protect the adhesive surface before use. The cover sheets may comprise a film of polyethylene, polypropylene or fluorocarbons and papers coated with these materials. Suitably, the cover sheet is a release-coated paper sheet, such as a silicone release-coated paper sheet. Examples of silicone-coated release papers are POLYSLIK (Registered Trade Mark) supplied by H.P. Smith & Co., offered in various formulations to control the degree of adhesion of the paper to the silicone coated substrate surface.

In certain embodiments, the cover sheets may comprise two or more parts, such as a first removable part having a first edge and a second removable part that meets the first part along the first edge. Suitably, along each of said edges where the parts meet, one of the parts is folded back to provide a folded-back margin, and the other part overlaps the said folded-back margin. This provides an easy-to-grasp margin on each part in the region of overlap to assist removal of the cover sheet by the care giver. In other embodiments, the cover sheets may comprise three parts, for example as described in detail in EP-A-0117632.

Figure 7:
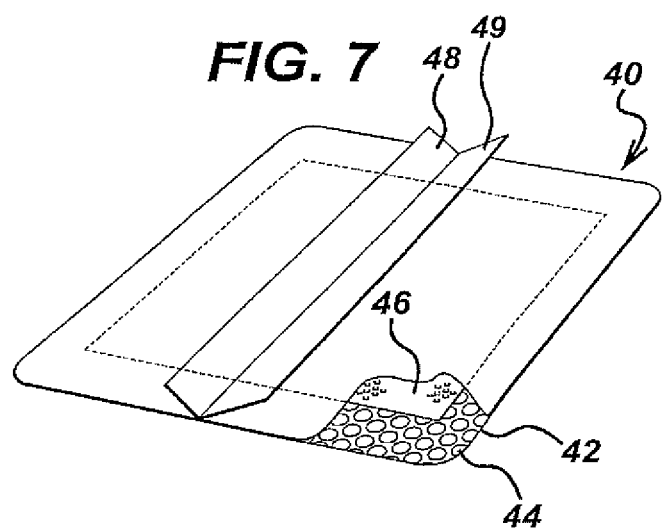
FIG. 7 shows a perspective view partially cut away of a wound dressing according to the present invention.

FIG. 7 shows a wound dressing according to this embodiment of the invention. The wound dressing 40 is an island-type dressing having a semipermeable polyurethane film backing sheet 42 that is the substrate for a printed pattern 44 of silicone adhesive. An absorbent island 46 of hydrophilic polyurethane foam is adhered centrally on the backing sheet by the silicone adhesive. Release coated cover sheets 48,49 are applied over the wound facing side of the dressing.

Figure 8:
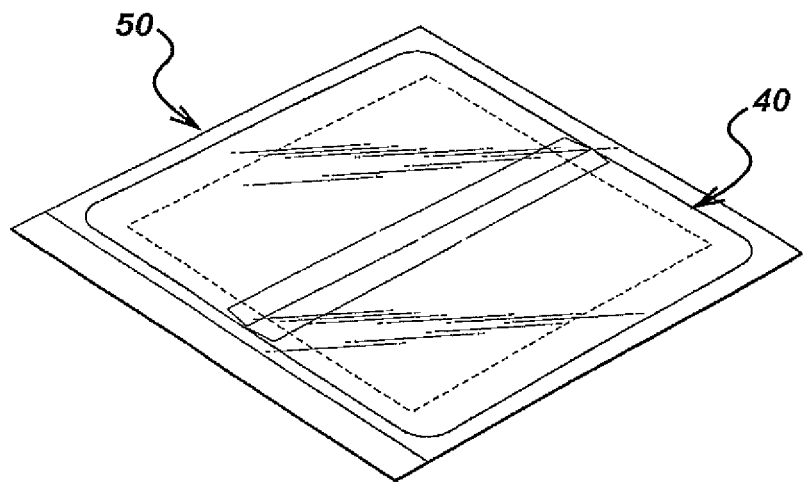
FIG. 8 shows the wound dressing of FIG. 7 packaged in a microorganism-impermeable container.

Suitably, the wound dressings of the invention are sterile and packaged in a microorganism-impermeable container, such as a pouch. FIG. 8 shows the wound dressing 40 of FIG. 7 packaged in a microorganism-impermeable pouch 50.

Any feature disclosed herein in relation to any one or more aspects of the invention may be present in any of the other aspects defined herein. Likewise, any combination of the alternative features described herein may be present in any of the aspects of the invention. It will be understood that all such combinations and features of the different aspects have not been described in detail herein solely for reasons of brevity.

EXAMPLE 1

A support mesh is coated with a fluid silicone adhesive prepolymer composition. The support mesh is a polypropylene sheet having a hexagonal (close packed) array of circular apertures of diameter 8 mm and open area about 60%. The silicone prepolymer is made by mixing Components Gel A and Gel B (Dow Corning products Q7-9177) at a weight ratio of 50:50 at 25-40° C. The mesh is coated by transferring of mixture using either a roller or a coating machine.

The silicone prepolymer composition on the support mesh is gently pressed onto substrate sheet formed of 0.4 mm high-density polyurethane foam formed from a blocked toluene di-isocyanate. The coated substrate with the mesh in place is then cured at 110-150° C. for 2 to 6 minutes. The support mesh is then lifted off to leave a pattern of adhesive on the support sheet corresponding to the pattern of lands on the support mesh This results in a substrate coated with a patterned silicone adhesive as shown in FIG. 6.

Moisture vapour transfer rate (MVTR) was measured for the resulting pattern coated adhesive sheets. For comparison, MVTR was also measured for the semipermeable substrate layer without any coating, and for the semipermeable substrate layer having a continuous coating of the same silicone adhesive. The results were as follows:

| Material | MVTR ($g/m^2/24$ hr) |
|---|---|
| Film Backing | 12002.5 |
| Film backing + continuous layer of silicone | 311 |
| Film backing + patterned layer of silicone | 8910.5 |

It can be seen that the silicone adhesive is substantially impermeable to moisture, but that this drawback can be substantially overcome by the use of the patterned adhesive coating.

EXAMPLE 2

The method of Example 1 is repeated with replacement of the semipermeable film substrate by a hydrophilic polyurethane foam substrate (TIELLE®, produced by Systagenix Wound Management). A similar printed adhesive pattern is achieved on the foam.

The above examples have been described by way of illustration only. Many other embodiments falling within the scope of the accompanying claims will be apparent to the skilled reader.

The invention claimed is:

1. A method of pattern coating a silicone adhesive onto a substrate sheet, comprising:
    coating a fluid silicone precursor composition onto an apertured support layer to provide a coated apertured support layer;
    applying the coated apertured support layer to an upper surface of a substrate sheet to apply a pattern of silicone precursor composition on the substrate sheet;
    wherein the pattern of silicone precursor composition on the substrate sheet is defined by one or more first portions comprising portions of the upper surface of the substrate sheet to which the fluid silicone prepolymer compositions has been applied and one or more second portions comprising portions of the upper surface of the substrate sheet to which no fluid silicone prepolymer composition has been applied;
    thermally curing the silicone precursor composition on the substrate sheet to leave a pattern of silicone adhesive on the substrate sheet; and
    removing the coated apertured support layer.

2. The method according to claim 1, wherein the one or more first portions of the pattern of silicone precursor composition corresponds to a pattern of lands formed in the apertured support layer and the one or more second portions of the pattern of silicone precursor composition corresponds to a pattern of holes formed in the apertured support layer.

3. The method according to claim 1, wherein the apertured support layer is a perforated sheet containing an array of perforations, the perforations having an area of at least about 4 $mm^2$.

4. The method according to claim 1, wherein the silicone precursor composition is substantially solvent-free.

5. The method according to claim 1, wherein the silicone precursor composition is applied to cover from about 10% to about 50% of a surface area of the substrate sheet.

6. The method according to claim 2, wherein the pattern of lands and holes comprises lands having a minimum dimension of about 2 mm.

7. The method according to claim 1, wherein the substrate sheet is a continuous semipermeable sheet having a moisture vapor transfer rate (MVTR) before coating of at least about 500 $g/m^2$/24 hr.

8. The method according to claim 1, wherein the apertured support layer has a surface that comprises a perfluorocarbon.

9. A method of applying a patterned coating of a silicone adhesive, comprising:
    providing a mold sheet having upper and lower surfaces extending between a top edge, a bottom edge, a left edge and a right edge, and a pattern of recesses in the upper surface;
    filling the recesses with a fluid silicone prepolymer composition;
    contacting the upper surface of the mold sheet with a substantially planar substrate sheet so that the substrate sheet contacts the fluid silicone prepolymer composition in the recesses, wherein the upper surface of the mold sheet as defined between the top edge, bottom edge, left edge and right edge of the mold sheet extends in a plane substantially parallel to a plane along which the substrate sheet extends upon application of the mold sheet to the substrate sheet;
    curing the silicone prepolymer composition in contact with the substrate sheet to form a silicone adhesive; and
    removing the substrate sheet and silicone adhesive from the mold sheet.

10. The method according to claim 9, wherein the thickness of the mold sheet is from about 0.1 mm to about 2 mm.

11. The method according to claim 9, wherein the step of curing the silicone prepolymer composition comprises thermal curing.

12. The method according to claim 9, wherein the recesses have a substantially constant depth of 0.5 mm.

13. A method of applying a patterned coating of a silicone adhesive, comprising:
    applying a fluid silicone prepolymer composition to an outside surface of an intaglio roller by a transfer roller to fill a plurality of recesses formed in the outside surface of the intaglio roller;

passing a blade along the outside surface of the intaglio roller to remove fluid silicone prepolymer composition not disposed in the recesses from the outside surface of the intaglio roller; and forming a substrate sheet upper surface pattern by applying the outside surface of the intaglio roller to a substrate sheet to apply the fluid silicone prepolymer composition to an upper surface of the substrate sheet, the resulting substrate sheet upper surface pattern being defined by one or more first portions comprising portions of the upper surface of the substrate sheet to which the fluid silicone prepolymer compositions has been applied;

wherein the substrate sheet upper surface pattern is further defined by one or more second portions comprising portions of the substrate sheet upper surface to which no fluid silicone prepolymer composition has been applied; and curing the fluid silicone prepolymer composition in contact with the substrate sheet to form a silicone adhesive.

14. The method according to claim 13, wherein the fluid silicone prepolymer composition is at least partially cured while the outside surface of the intaglio roller is in contact with the substrate sheet.

15. The method according to claim 13, wherein the step of curing the fluid silicone prepolymer composition comprises thermal curing.

16. A method of applying a patterned coating of a silicone adhesive, comprising:
providing a mold sheet having upper and lower surfaces and a pattern of apertures extending between the upper and lower surfaces;
filling the apertures with a fluid silicone prepolymer composition;
contacting one of the upper or lower surfaces with a first surface of a substrate sheet so that one or more first portions of the first surface of the substrate sheet contact the fluid silicone prepolymer composition in the apertures, while one or more second portions of the first surface of the substrate sheet do not contact the fluid silicone prepolymer composition in the apertures;
curing the fluid silicone prepolymer composition in contact with the one or more first portions of the first surface of the substrate sheet to form a pattern defined by a plurality of silicone adhesive segments;
wherein adjacent silicone adhesive segments are separated from one another by one or more second portions of the first surface of the substrate sheet; and
removing the mold sheet.

17. The method according to claim 16, wherein the thickness of the mold sheet is from about 0.1 mm to about 2 mm.

18. The method according to claim 16, wherein the step of curing the fluid silicone prepolymer composition comprises thermal curing.

19. A method of applying a patterned coating of a silicone adhesive, comprising:
providing a screen printing roller formed from a mold sheet material and having a plurality of apertures;
delivering a fluid silicone prepolymer composition to a first channel inside of the screen printing roller to feed the fluid silicone prepolymer composition selectively to a first group of apertures of the screen printing roller that are in contact with a substrate sheet;
feeding a compressed gas through a second channel that surrounds the first channel to apply an outward force on the fluid silicone prepolymer composition in the apertures towards the substrate sheet;
rotating the screen printing roller to allow a second group of apertures to be filled with the fluid silicone prepolymer composition as the substrate sheet moves past the screen printing roller; and
curing the silicone prepolymer composition in contact with the substrate sheet.

20. The method according to claim 19, wherein the step of curing the fluid silicone prepolymer composition comprises thermal curing.

21. A method of applying a patterned coating of a silicone adhesive, comprising:
providing a screen printing roller formed from a mold sheet material and having a plurality of apertures;
delivering a fluid silicone prepolymer composition to a first channel inside of the screen printing roller to feed the fluid silicone prepolymer composition selectively to a first group of apertures of the screen printing roller that are in contact with a substrate sheet;
rotating the screen printing roller to allow a second group of apertures to be filled with the fluid silicone prepolymer composition as the substrate sheet moves past the screen printing roller;
wherein an edge of the first channel acts as a blade to wipe an inside surface of the screen printing roller after the apertures have been filled with the fluid silicone prepolymer composition; and
curing the silicone prepolymer composition in contact with the substrate sheet.

* * * * *